United States Patent [19]

Hite et al.

[11] Patent Number: 5,130,485
[45] Date of Patent: Jul. 14, 1992

[54] N-HYDROXY-N-(3-(2-SUBSTITUTED PHENYL)PROP-2-ENYL)UREAS AND THIOUREAS USEFUL AS 5-LIPOXYGENASE INHIBITING AGENTS

[75] Inventors: Gary A. Hite, Indianapolis; Edward D. Mihelich, Carmel; David W. Snyder, Indianapolis; Tulio Suarez, Greenwood, all of Ind.

[73] Assignee: Eli Lilly and Company, Indianapolis, Ind.

[21] Appl. No.: 690,131

[22] Filed: Apr. 23, 1991

[51] Int. Cl.$^5$ .................. C07C 275/64; A61K 31/17
[52] U.S. Cl. .................. 562/623; 514/825; 514/826; 514/863; 514/882; 514/885
[58] Field of Search ............. 562/623; 514/575, 595, 514/863, 882, 885, 587, 825, 826

[56] References Cited

U.S. PATENT DOCUMENTS 4,738,986  4/1988  Kneen et al. ................ 514/575

FOREIGN PATENT DOCUMENTS

| 196184 | 10/1986 | European Pat. Off. . |
| 279263 | 8/1988 | European Pat. Off. . |
| 279281 | 8/1988 | European Pat. Off. . |
| 292699 | 11/1988 | European Pat. Off. . |
| 0384594 | 8/1990 | European Pat. Off. ............ 562/623 |
| WO90/12008 | 10/1990 | PCT Int'l Appl. . |
| 2196629 | 5/1988 | United Kingdom . |

OTHER PUBLICATIONS

R. A. Hahn et al., *J. Pharmocol. Exp. Ther.*, 256, 94–102 (1991).

*Primary Examiner*—Jose G. Dees
*Assistant Examiner*—B. Frazier
*Attorney, Agent, or Firm*—John C. Demeter; Leroy Whitaker

[57] ABSTRACT

This invention relates to N-hydroxy-N-[3-(2-substituted phenyl)prop-2-enyl]ureas and thioureas, formulations containing those compounds, and methods of using such compounds as 5-lipoxygenase inhibiting agents.

22 Claims, No Drawings

N-HYDROXY-N-(3-(2-SUBSTITUTED PHENYL)PROP-2-ENYL)UREAS AND THIOUREAS USEFUL AS 5-LIPOXYGENASE INHIBITING AGENTS

BACKGROUND OF THE INVENTION

This invention relates to N-hydroxy-N-[3-(2-substituted phenyl)prop-2-enyl]ureas and thioureas, compositions containing those compounds and methods of their use.

The enzyme 5-lipoxygenase (5-LO) catalyzes the first step of a biochemical synthesis pathway by which arachidonic acid is converted into leukotrienes. Numerous and extremely potent biological activities have been associated with leukotrienes. Leukotrienes have been implicated as important mediators in a variety of disease states such as asthma, ischemia, arthritis, psoriasis, allergy, adult respiratory distress syndrome (ARDS) and inflammatory bowel disease (IBD).

Considerable efforts have been directed toward the control of leukotrienes by means of leukotriene antagonists or by control of leukotriene biosynthesis. Generally, research efforts directed toward the control of leukotriene biosynthesis have been directed toward the discovery of inhibitors of the 5-LO pathway and, in particular, 5-LO specific inhibitors.

In U.K. Patent Application GB 2,196,629 certain ring substituted-N-hydroxy-N-substituted benzamide and cinnamamide compounds are disclosed as antileukotriene agents. The ring substituent may be a group having the Formula (Ra) (Rb) C=CH— where (Ra) (Rb) C= is an unsaturated aliphatic hydrocarbylene group containing 3 to 19 carbon atoms; a group having the Formula $R_3$-C≡C— where $R_3$ is a hydrogen atom or a saturated or unsaturated aliphatic hydrocarbyl group containing 1 to 18 carbon atoms; or a group having the Formula $R_4$-S— where $R_4$ is an aliphatic hydrocarbyl group containing 1 to 20 carbon atoms. The N-substituent may be a $C_1$-$C_6$ alkyl group, a $C_3$-$C_7$ cycloalkyl group or a substituted or unsubstituted aryl group.

In European Patent Application 0 196 184 certain aryl compounds are disclosed which include, among many others, certain cinnamohydroxamic acid analogs. Also included are certain N-aryl-N-hydroxy ureas in Examples 81-91.

In European Patent Application 0 292 699 certain urea based lipoxygenase inhibiting compounds are disclosed. These ureas include certain N-hydroxy-N-((phenyl or naphthyl or thienyl)alkyl)ureas.

In WO 90/12008 certain unsubstituted and substituted phenyl, naphthyl and thienyl N-hydroxy ureas are disclosed as inhibitors of 5- and 12-lipoxygenase. The preparation and biological activity for a number of such derivatives is disclosed.

The present invention is directed to the discovery that N-hydroxy-N-[3-(2-substituted phenyl)prop-2-enyl]ureas and thioureas, where said 2-position substituent is a hydrocarbylthio group or hydrocarbyloxy group and the hydrocarbyl radical has one or more unsaturated linkages, are potent 5-LO inhibitors. The compounds of the present invention, as defined below, are surprisingly advantageous inhibitors of 5-LO and have useful medical prophylactic and therapeutic properties. The compounds of the present invention and their pharmaceutically acceptable salts possess particularly high potency.

Accordingly, it is a primary object of the present invention to provide novel N-hydroxy-N-[3-(2-substituted phenyl)prop-2-enyl]ureas and thioureas which are potent selective 5-LO inhibitors useful in the treatment of asthma and allergic diseases, inflammatory bowel disease, ischemia, psoriasis, shock, adult respiratory distress syndrome (ARDS), and arthritis.

A further object of the present invention is to provide therapeutic compositions for treating said diseases and disorders.

Still another object is to provide methods for treating said diseases and disorders.

Other objects, features and advantages will become apparent to those skilled in the art from the following description and claims.

SUMMARY OF THE INVENTION

The present invention provides novel N-hydroxy-N-[3-(2-substituted phenyl)prop-2-enyl]ureas and thioureas of the Formula

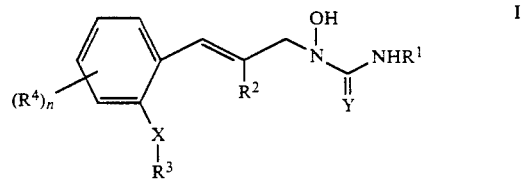

where
X is O or S;
Y is O or S;
$R^1$ is hydrogen, $C_1$-$C_4$ alkyl or $C_3$-$C_8$ cycloalkyl;
$R^2$ is hydrogen or methyl;
$R^4$ is hydrogen or halo;
n is 1 or 2;
$R^3$ is $C_2$-$C_{12}$ alkenyl, $C_3$-$C_{12}$ alkadienyl, $C_4$-$C_{12}$ alkatrienyl, $C_2$-$C_{12}$ alkynyl, $C_4$-$C_{12}$ alkenynyl, $C_3$-$C_8$ cycloalkylemthyl, unsubstituted or substituted styryl, or unsubstituted or substituted phenylethynyl where the phenyl ring of styryl and phenylethynyl may be substituted with one, two, or three of the same or different halo, hydroxy $C_1$-$C_4$ alkyl, $C_1$-$C_4$ alkoxy, $C_1$-$C_4$ alkylthio, trifluoromethyl or trifluoromethoxy and pharmaceutically acceptable salts thereof.

In addition to the compounds of Formula I, the present invention provides pharmaceutical formulations comprising a compound of Formula I in association with a pharmaceutically acceptable carrier, diluent or excipient.

The present invention also provides a method of treating asthma, allergic diseases, inflammatory bowel disease, psoriasis, ischemia, shock, ARDS and arthritis in mammals comprising administering to a mammal in need of such treatment an effective amount of a compound according to Formula I.

DETAILED DESCRIPTION OF THE INVENTION

The term "alkyl" by itself or as part of another substituent, means a straight or branched chain alkyl radical having the stated number of carbon atoms such as methyl, ethyl, n-propyl, isopropyl, n-butyl, t-butyl, isobutyl and sec-butyl.

The term "cycloalkyl" means a cyclic alkyl radical having the stated number of carbon atoms such as cyclopropyl, cyclobutyl, cyclopentyl, cyclohexyl, cycloheptyl and cyclooctyl.

The term "halo" means any one of chloro, fluoro, bromo or iodo.

The term "$C_2$-$C_{12}$ alkenyl" means an unsaturated hydrocarbon group having the stated number of carbon atoms and a single carbon-carbon double bond such as ethenyl, 1-propenyl, 2-propenyl, 1-butenyl, 2-butenyl and the like.

The term "alkadienyl" means an unsaturated aliphatic hydrocarbon group having the state number of carbon atoms and two carbon-carbon double bonds which may be isolated, conjugated or cumulated. Such alkadienyl groups include 1,4-pentadienyl, 1,5-hexadienyl, 1,3-butadienyl, 1,3-pentadienyl and 1,2-propadienyl.

Similarly, the term "alkatrienyl" means an unsaturated aliphatic hydrocarbon group having the stated number of carbon atoms and three carbon-carbon double bonds which may be isolated, conjugated, cumulated or a combination thereof. Such alkatrienyl groups include 1,3,5-hexatrienyl.

The term "alkynyl" means an unsaturated hydrocarbon group having the stated number of carbon atoms and a single carbon-carbon triple bond such as ethynyl, 1-propynyl, 1-butynyl, 1-pentynyl, 1-hexynyl, 1-heptaynyl, 1-octynyl, 1-nonynyl, 1-decynyl, 2-butynyl, 2-pentynyl, 2-hexynyl, 3-hexynyl, 4-octynyl and 5-decynyl.

The term "alkenynyl" means an unsaturated hydrocarbon group having the stated number of carbon atoms with one or two carbon-carbon double bonds and one carbon-carbon triple bond. Such groups include 2,4-octadien-6-ynyl, 3-ethynyl-1,4-pentadienyl, 1,3-hexadien-5-ynyl, 3-penten-1-ynyl and 1-penten-4-ynyl.

The term "phenylethynyl" means a group $C_6H_5C\equiv C-$.

The term "alkoxy" means an alkyl group having the stated number of carbon atoms linked to the parent molecular moiety by an oxygen atom. Similarly, "alkylthio" means an alkyl group having the stated number of carbon atoms linked to the parent molecular moiety by a sulfur atom.

The following compounds illustrate compounds contemplated within the scope of Formula I:

N-hydroxy-N-[3-[2-(2-propynythio)phenyl]prop-2-enyl]urea.
N-hydroxy-N-[3-[2-(2-butynylthio)phenyl]prop-2-enyl]urea.
N-hydroxy-N-[3-[2-(3-butynylthio)phenyl]prop-2-enyl]urea.
N-hydroxy-N-[3-[2-(3-butenylthio)phenyl]prop-2-enyl]urea.
N-hydroxy-N-[3-[2-(cyclohexylmethylthio)phenyl]-prop-2-enyl]urea.
N-hydroxy-N-[3-[2-(cyclopropylmethylthio)phenyl]-prop-2-enyl]urea.
N-hydroxy-N-[3-[2-(2-propynyloxy)phenyl]prop-2-enyl]urea.
N-hydroxy-N-[2-methyl-3-[2-(2-propynylthio)phenyl]-prop-2-enyl]urea.
N-hydroxy-N-[3-[3-fluoro-2-(2-propynylthio)phenyl]-prop-2-enyl]urea.

Preferred compounds of Formula I are those where:
X is S;
Y is O;
$R^1$ is hydrogen or $C_1$-$C_4$ alkyl;
$R^2$ is hydrogen;
$R^4$ is hydrogen or halo;
n is 1 or 2;
$R^3$ is $C_2$-$C_{12}$ alkynyl, or $C_3$-$C_6$ cycloalkylmethyl; and pharmaceutically acceptable salts thereof.

As mentioned above, the invention includes pharmaceutically acceptable salts of the compounds defined by Formula I. Although generally neutral, a particular compound of this invention can possess a sufficiently acidic or basic functional group to react with any of a number of nontoxic inorganic bases, and nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluene-sulfonic, methanesulfonic acid, oxalic acid, p-bromo-phenyl-sulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, chloride, bromide, iodide, acetate, propinate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

The compounds of the present invention or their precursors can be prepared according to the follow processes.

Scheme 1:

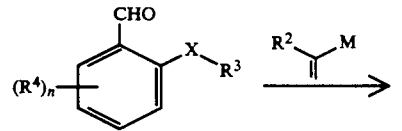

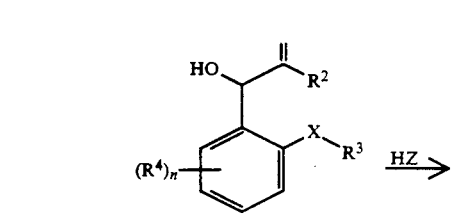

Scheme 1:

-continued

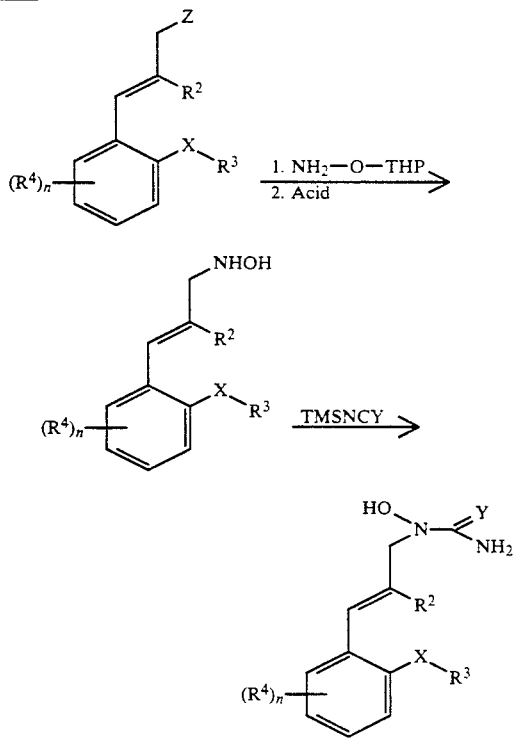

where
X, Y, R² , R³ and R⁴ are as defined above for Formula 1,
Z is halo, preferably chloro or bromo,
M is Li or MgBr.

In Scheme 1, a 2-substituted benzaldehyde is reacted with an allyl or vinyl Grignard reagent, or an allyl or vinyl lithium reagent in an inert or substantially inert solvent or mixture of solvents to afford the corresponding 1-hydroxy-1-(2-substituted phenyl)prop-2-ene which may be isolated or further reacted as described below. This reaction is carried out under standard conditions for a Grignard reaction which are known to those skilled in the art. When an allyl or vinyl lithium reagent is used, this reagent is preferably prepared in situ by reacting an allyl or vinyl bromide with two equivalents of t-butyllithium at about −78° C. in an ether solvent, preferably THF, to afford the corresponding lithio reagent. This lithio reagent is then reacted with the 2-substituted benzaldehyde in an ether solvent, preferably THF, at a temperature of from about −100° C. to about −40° C., preferably from about −60° C. to about −85° C., to afford the corresponding 1-hydroxy-1-(2-substituted phenyl)prop-2-ene.

The 1-hydroxy-1-(2-substituted phenyl)prop-2-ene is reacted with a concentrated acid, preferably HCl or HBr, in an inert or substantially inert solvent or mixture of solvents to afford a 2-substituted cinnamyl halide. Aprotic solvents are generally suitable and preferably ether.

The 2-substituted cinnamyl halide is reacted with N-(O-tetrahydropyranylhydroxyl)amine in an inert or substantially inert solvent or mixture of solvents to afford the corresponding N-(2-substituted cinnamyl)-N-(O-tetrahydropyranylhydroxyl)amine which can be isolated or further reacted with an acid, preferably concentrated HCl, in an inert or substantially inert solvent or mixture of solvents to afford the corresponding N-(2-substituted cinnamyl)-N-hydroxylamine.

Suitable solvents for these reactions are aprotic solvents, preferably dimethylformamide. These reactions are carried out at temperatures of from about 0° C. to about 50° C. and preferably at about room temperature. The deprotection step is generally carried out in protic solvents and preferably methanol.

The N-(2-substituted cinnamyl)-N-hydroxylamine is reacted with a trimethylsily isocyanate or trimethylsilyl isothiocyanate in an inert or substantially inert solvent or mixture of solvents to afford the desired compound of Formula I.

Suitable solvents for the isocyanate or isothiocyanate condensation include ethers and preferably dioxane. This reaction can be carried out at temperature of from about 0° C. to about 50° C. and preferably at about room temperature.

The N-(O-tetrahydropyranylhydroxyl)amine is prepared according to procedures described in *Agnew. Chem. Int. Ed.*, 5, 511 (1966). The 2-substituted benzaldehydes in Scheme 1, to the extent they are not commercially available, are obtained by the routes shown below in Schemes 2 and 3, using procedures well-known to those skilled in the art.

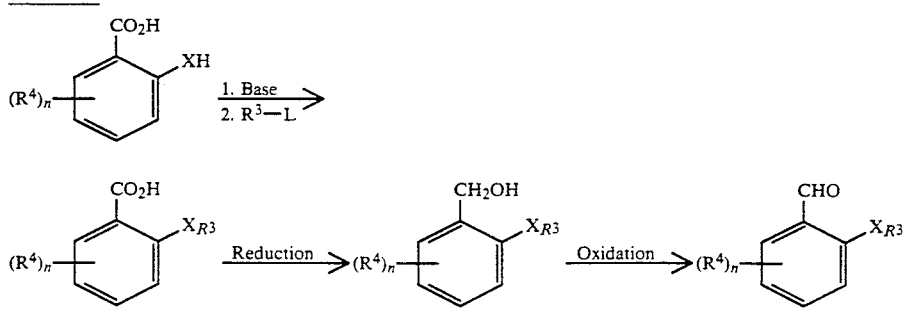

Scheme 2:

Scheme 2:

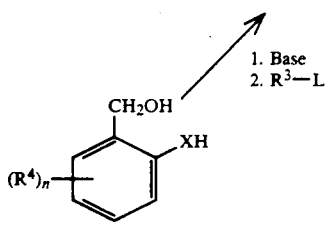

where:
R³, R⁴, n and X are as defined above for Formula I; and
L is a leaving group, such as halo, mesylate, tosylate, or triflate.

Scheme 3:

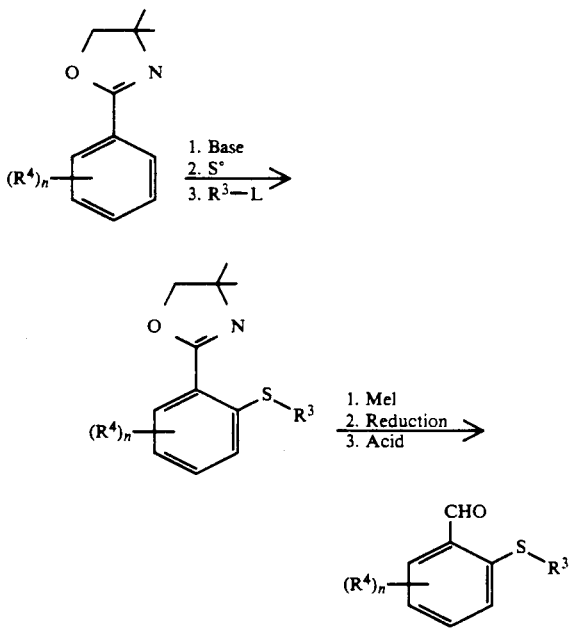

where:
R³, R⁴, and n are as defined above for Formula I; and
L is a leaving group as defined above for Scheme 2.

In Scheme 2, a 2-hydroxy or 2-mercapto carboxylic acid is reacted with a base, preferably a mild inorganic base such as $K_2CO_3$, in a suitable inert or substantially inert solvent or mixture of solvents and then alkylated with a compound having the formula R³-L where R³ is as defined above for Formula I and L is a leaving group such as halo, mesylate, tosylate or triflate, in a suitable inert or substantially inert solvent or mixture of solvents to afford the corresponding 2-substituted carboxylic acid which may be isolated or further reacted as described below.

Suitable solvents for those reactions are aprotic such as methyl ethyl ketone. These reactions are carried out at temperatures of from about −20° C. to about 50° C.

The 2-substituted benzoic acid intermediate is then reacted with a reducing agent, preferably a hydride and particularly $LiAlH_4$, in an aprotic solvent such as ethers and preferably diethyl ether at a temperature of from about −20° C. to about 50° C. to afford the corresponding 2-substituted benzyl alcohol which may be isolated or further reacted as described below.

Alternatively, a 2-hydroxy or mercapto benzyl alcohol can be alkylated, following the procedures described above for alkylating the 2-hydroxy or 2-mercapto benzoic acid compound, to afford the 2-substituted benzyl alcohol.

The 2-substituted benzyl alcohol is oxidized with pyridinium dichromate or pyridinium chlorochromate in a suitable polar aprotic solvent such as haloalkanes and preferably methylene chloride, at a temperature of from about 10° C. to about 50° C., preferably at room temperature, to afford the 2-substituted benzaldehyde intermediate which may be isolated or further reacted according to Scheme 1.

In Scheme 3, a 2-phenyl-4,4-dimethyloxazoline is reacted with a base, preferably a $C_1-C_4$ alkyl lithium base, and particularly n-butyllithium, to activate the ortho position on the phenyl rings and then reacted with elemental sulfur, followed by alkylation with a compound having the formula R³-L where R³ is as defined above for Formula I and L is a leaving group such as halo, mesylate, tosylate or triflate, in a suitable inert or substantially inert solvent or mixture of solvents at a temperature of from about −60° C. to about 50° C. to afford the corresponding 2-(2-substituted phenyl)-4,4-dimethyloxazoline which may be isolated or further reacted as described below.

Suitable solvents for these reactions are generally aprotic, preferably ethers, and particularly THF.

The 2-(2-substituted phenyl)-4,4-dimethyloxazoline intermediate is then reacted with methyl iodide to quaternize the oxazoline followed by reduction with a hydride reducing agent, preferably, sodium borohydride, and then hydrolyzed with acid to afford a 2-substituted benzaldehyde which may be isolated or further reacted as described in Scheme 1.

Temperatures for these reactions vary from about room temperature for quaternization, to from about −20° C. to about 30° C. for the reduction and the hydrolysis. Suitable solvents for these reactions are polar aprotic, such as alcohols and preferably ethanol. The hydrolysis is carried out using an inorganic acid, preferably 2N HCl.

To the extent not commercially available, the initial compounds for Schemes 2 and 3 can be prepared by reactions both apparent and well known to those skilled in the art. Such reactions include, but are not limited to, reacting benzoic acid, bromobenzoic acid, anisic acid or other optionally substituted benzoic acid with 2-amino-2-methyl-1-propanol to afford the corresponding 2-oxazoline. To the extent not already present, the desired -X-R³ substituent or substituents can then be added to the phenyl ring through reactions which are both apparent and well known to those skilled in the art such as alkylation, Grignard addition or coupling, silation-desilation, and the like, including combinations of such reactions. The conditions for such reactions are well known or readily ascertained by those skilled in the art.

The phrase "inert or substantially inert solvent or mixture of solvents" are substances that provide a medium in which a reaction can occur but otherwise do not materially contribute to the reaction.

Modifications to the above processes may be necessary to accommodate the reactive functionalities of particular substitutents. Such modifications would be both apparent and known to those skilled in the art.

It is recognized that various isomeric forms of the compounds of Formula I may exist. This invention is not limited to any particular isomer but rather includes all possible individual isomers and mixtures thereof.

The compounds of Formula I and the pharmaceutically acceptable salts thereof can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent. These solvates are also within the scope of the present invention.

The pharmaceutically acceptable salts embraced by Formula I of the present invention are prepared by reacting an equimolar or excess amount of an acid or base with a compound of Formula I in a suitable mutual inert or substantially inert solvent or a mixture of solvents. The particular choice of solvent will depend on the relative solubility of the starting materials and resultant salts, and slurries rather than solutions of certain reagents may be used to obtain the salts. The salt forming reaction is carried out at about −10° C. to about 100° C., preferably about room temperature and the solvent is removed by conventional means.

The following examples will further illustrate this invention but are not intended to limit it in any way.

Example 1

Preparation of N-hydroxy-N-[3-[2-(2-propynylthio)phenyl]prop-2-enyl]urea.

A. 2-(2-propynylthio)benzoic acid

To thiosalicylic acid (77 g) slurried in methyl ethyl ketone (500 ml) was added 1 equivalent of $K_2CO_3$ followed by 3-bromopropyne (1 equivalent). The reaction mixture was stirred for 3 hours and then poured into 1N HCl and the solids filtered and then vacuum dried to afford the subtitle compound.

B. 2-(2-propynylthio)benzyl alcohol

To a slurry of $LiAlH_4$ (6.5 g; 0.17 mmol) in 250 ml of tetrahydrofuran (THF) at 0° C. was added 2-(2-propynylthio)benzoic acid (28.8 g; 0.15 mmol). The reaction mixture was allowed to warm to room temperature. To the reaction mixture was added 6.5 ml of water, then 6.5 ml of 15% NaOH and 13.0 ml of water. The mixture was filtered through diatomaceous earth (Celite,) and concentrated to afford 22 g of the subtitle compound.

C. 2-(2-propynylthio)benzaldehyde

To $CH_2Cl_2$ was added the benzyl alcohol (22 g) from Step B, above and then pyridinium chlorochromate (30.75 g; 0.15 mmol). The reaction mixture was stirred at room temperature for 2 hours then filtered and concentrated to afford 12.0 g of the subtitle compound. Several lots of the subtitle compound were prepared according to the procedures of Step A, B, and C, and were combined to afford 35.2 g of the subtitle compound.

D. 1-[2-(2-propynylthio)phenyl]prop-2-en-1-ol

To 35.2 g of 2-(2-propynylthio)benzaldehyde in dry THF cooled to between −60° and −70° C. was added 210 ml of a 1M solution of vinylmagnesium bromide solution dropwise at −60° C. and the reaction mixture allowed to warm to room temperature. The reaction mixture was poured into saturated $NH_4Cl$ and extracted twice with diethyl ether. The extracts are washed with water and then brine and dried over $MgSO_4$ to afford 42.1 g of the subtitle compound.

E. 1-[2-(2-propynylthio)phenyl]-3-bromoprop-1-ene

The propen-1-ol (42 g; 0.2 mmol) from Step D, above, was added to 320 ml of a 2:1 (v:v) mixture of ether and hexane and 70 ml of concentrated HBr was added dropwise. The reaction mixture was stirred overnight. The reaction mixture was poured into water and extracted twice with diethyl ether. The extracts are washed with water and then brine and dried over $MgSO_4$ to afford 50 g of the subtitle compound.

F. N-[3-[2-(2-propynylthio)phenyl]prop-2-enyl]-O-tetrahydropyranylhydroxylamine

O-tetrahydropyranylhydroxylamine (65 g) is dissolved in 200 ml of dry DMF, and a solution of the cinnamyl bromide 50.9 g prepared above in Step E in 100 ml of DMF are combined and the reaction mixture is stirred for 2 hours at room temperature. The reaction mixture is poured into water and extracted twice with diethyl ether. The extracts are washed three times with water and then with brine and dried over $MgSO_4$ to afford the crude subtitle compound. Chromatography on silica gel eluting with 5:1 hexane/ethyl acetate afforded 36 g of the subtitle compound.

G. N-[3-[2-(2-propynylthio)phenyl]prop-2-enyl]hydroxylamine

To the tetrahydropyranylhydroxylamine (36.0 g) prepared above in Step F, in 250 ml methanol and cooled in an ice bath was added 25 ml of concentrated HCl dropwise. The reaction mixture was stirred overnight at room temperature. The reaction mixture was concentrated and the residue slurried in saturated $NaHCO_3$ solution and then extracted twice with diethyl ether. The extracts were washed with water and then brine and dried over $K_2CO_3$ to afford 24.6 g of the subtitle compound.

H. N-hydroxy-N-[3-[2-(2-propynylthio)phenyl]prop-2-enyl]urea

To the N-hydroxylamine prepared above in Step G, in 300 ml of dry dioxane was added dropwise 16.2 ml of trimethylsilyl isocyanate and the reaction mixture stirred at room temperature overnight. The reaction mixture was poured into water and extracted twice with ethyl acetate. The extracts were washed with water and then brine, dried over $MgSO_4$ and concentrated to afford the crude subtitle compound. Recrystallization from hot ethyl acetate afforded 15.6 g of the subtitle compound. m.p. 141°-142° C.

Analysis Calculated for $C_{13}H_{14}N_2O_2S$:

|  | C | H | N |
|---|---|---|---|
| Calculated: | 59.52 | 5.38 | 10.68 |
| Found: | 59.29 | 5.28 | 10.47 |

By substantially following the procedures described above in Example 1 the compounds of Examples 2, 3, 4, 5 and 6 were prepared.

EXAMPLE 2

N-hydroxy-N-[3-[2-(3-butynylthio)phenyl]prop-2-enyl]urea 1.14 g; mp 108°-109° C.
Elemental Analysis

|  | C | H | N | S |
|---|---|---|---|---|
| Calculated: | 60.85 | 5.84 | 10.14 | 11.60 |
| Found: | 60.60 | 5.66 | 9.88 | 11.87 |

EXAMPLE 3

N-hydroxy-N-[3-[2-(2-butynylthio)phenyl]prop-2-enyl]urea 1.07 g; mp 132°-133.5° C.
Elemental Analysis

|  | C | H | N | S |
|---|---|---|---|---|
| Calculated: | 60.85 | 5.84 | 10.14 | 11.60 |
| Found: | 61.15 | 5.96 | 10.08 | 11.45 |

EXAMPLE 4

N-hydroxy-N-[3-[2-(3-butenylthio)phenyl]-prop-2-enyl]urea m.p. 96°-98° C.
Elemental Analysis

|  | C | H | N | S |
|---|---|---|---|---|
| Calculated: | 60.41 | 6.52 | 10.06 | 11.52 |
| Found: | 60.55 | 6.37 | 9.86 | 11.47 |

EXAMPLE 5

N-hydroxy-N-[3-[2-(cyclohexylmethylthio)phenyl]-prop-2-enyl]urea m.p. 140.5°-142° C.
Elemental Analysis

|  | C | H | N | S |
|---|---|---|---|---|
| Calculated: | 63.72 | 7.55 | 8.74 | 10.00 |
| Found: | 63.79 | 7.58 | 8.71 | 9.91 |

EXAMPLE 6

N-hydroxy-N-[3-[2-(cyclopropylmethylthio)phenyl]-prop-2-enyl]urea m.p. 115°-116.5° C.
Elemental Analysis

|  | C | H | N | S |
|---|---|---|---|---|
| Calculated: | 60.41 | 6.52 | 10.06 | 11.52 |
| Found: | 60.34 | 6.80 | 10.02 | 11.70 |

EXAMPLE 7

Preparation of N-hydroxy-N-[3-[2-(2-propynyloxy)phenyl]prop-2-enyl]urea

A. 2-(2-propynyloxy)benzyl alcohol

To 2-(hydroxymethyl)phenol (10.0 g, 80.6 mmol) slurried in 300 ml of methyl ethyl ketone was added 1.2 equivalents of potassium carbonate. Then 3-bromopropyne (121 mmol, 18 g of an 80% solution in toluene) and potassium iodide (0.5 g) were added and the reaction was refluxed overnight. After cooling the salts were filtered off. The filtrate was concentrated and the residue was dissolved in water and extracted twice with ether. After washing with water and brine, the organic layer was dried over $MgSO_4$ and concentrated to afford the subtitle compound.

B.
N-hydroxy-N-[3-[2-(2-propynyloxy)phenyl]prop-2-enyl]urea

By substantially following the procedures described above in Example 1, Steps C to the end, the subtitle compound was afforded. mp 117.5°-118.5° C.
Elemental Analysis

|  | C | H | N |
|---|---|---|---|
| Calculated: | 63.40 | 5.73 | 11.38 |
| Found: | 63.17 | 5.78 | 11.15 |

EXAMPLE 8

Preparation of N-hydroxy-N-[2-methyl-3-[2-(2-propynylthio)phenyl]-prop-2-enyl]urea A.
2-methyl-1-[2-(2-propynylthio)phenyl]prop-2-en-1-ol To 2-bromopropene (4.53 g, 37.4 mmol) in 85 ml of dry THF at −78° C. was added t-butyllithium (44 ml of a 1.7M solution in pentane) dropwise. After 2 hours, 2-(2-propynylthio) benzaldehyde (3.0 g, 17.0 mmol) prepared according to the procedures described in Example 1, Steps A, B, and C in 30 ml of dry THF was added dropwise. The reaction mixture was allowed to warm up to room temperature (RT). The reaction mixture was quenched with 100 ml of a saturated $NH_4Cl$ solution, extracted twice with diethyl ether, washed with water and brine, and then dried over $K_2CO_3$ to afford the subtitle compound.

B.
N-hydroxy-N-[2-methyl-3-[2-(2-propynylthio)phenyl]-prop-2-enyl]urea

By substantially following the procedures described above in Example 1, Steps E to the end, the subtitle compound was afforded. mp 82°-86° C.
Elemental Analysis

|             | C     | H    | N     | S     |
| ----------- | ----- | ---- | ----- | ----- |
| Calculated: | 60.85 | 5.84 | 10.14 | 11.60 |
| Found:      | 60.99 | 6.03 | 9.92  | 11.45 |

EXAMPLE 9

Preparation of
N-hydroxy-N-[3-[3-fluoro-2-(2-propynylthio)phenyl]-prop-2-enyl]urea

A. 2-[2-(2-propynylthio)-3-fluorophenyl]-4,4-dimethyloxazoline

To 2-(3-fluorophenyl-4,4-dimethyloxazoline (10.95 g, 56.7 mmol) in 190 ml of dry THF at −78° C. was added dropwise n-butyllithium (41 ml of a 1.6M solution in hexane). After stirring for 30 minutes, 1.15 equivalents of sulfur was added in four portions. After allowing the reaction mixture to warm to −25° C., it was cooled again to −78° C. and 3-bromopropyne (68 mmol, 10.1 g of an 80% solution in toluene) was added dropwise in 50 ml of dry THF. After allowing the reaction mixture to warm to RT, it was poured into 200 ml of a saturated $NH_4Cl$ solution and extracted twice with ether. The organic layer was washed with water and then brine and dried over $MgSO_4$ to afford the crude product. Chromatography over silica gel with 5:1 hexane/ethyl acetate and then 3:1 hexane/ethyl acetate afforded the subtitle compound.

B. 2-(2-propynylthio)-3-fluorobenzaldehyde

To the oxazoline from Step A (7.4 g, 28.1 mmol) in 10 ml of methylene chloride was added 10 ml of methyl iodide. After 5 days, the mixture was concentrated and then dissolved in 70 ml of methylene chloride and treated dropwise with sodium borohydride (1.28 g, 33.7 mmol) in 70 ml of ethanol. The reaction mixture was stirred overnight at RT and then poured into one liter of water and extracted twice with diethyl ether. The extracts were washed with water and then brine and dried over $K_2CO_3$ to afford the crude product. This crude product was dissolved in 95 ml of THF and then treated with 95 ml of a 2N HCl solution. The reaction mixture was then concentrated and extracted with ether. The organics were then washed with water and brine and dried over $MgSO_4$ to afford the subtitle compound.

C. N-hydroxy-N-[3-[3-fluoro-2-(2-propynylthio)phenyl]-prop-2-enyl]urea

By substantially following the procedures described above in Example 1, Steps D to the end, the subtitle compound was afforded. mp 136°–138° C.

Elemental Analysis

|             | C     | H    | N    | S     | F    |
| ----------- | ----- | ---- | ---- | ----- | ---- |
| Calculated: | 55.70 | 4.67 | 9.99 | 11.44 | 6.78 |
| Found:      | 55.73 | 4.74 | 9.70 | 11.67 | 7.08 |

By following the procedures described above and exemplified in the Examples, one skilled in the art can prepare the compounds of Formula I.

As noted above, the compounds of the present invention are useful for inhibiting the conversion of arachidonic acid by 5-lipoxygenase to 5-hydroperoxy-6,8,11,14-eicosatetraenoic acid (5-HPETE). Therefore, another embodiment of the present invention is a method for inhibiting the conversion of arachidonic acid into leukotrienes which comprises administering to a mammal in need of 5-lipoxygenase inhibition a 5-lipoxygenase inhibiting dose of a compound according to Formula I or a pharmaceutically acceptable salt thereof.

The term "effective amount" as used herein, means an amount of a compound of the present invention which is capable of inhibiting the first step of the biochemical synthesis pathway by which arachidonic acid is converted into leukotrienes which is catalyzed by the enzyme 5-lipoxygenase and particularly, inhibiting 5-lipoxygenase. The 5-lipoxygenase inhibition contemplated by the present method includes both medical therapeutic and/or prophylactic treatment, as appropriate. The specific dose of compound administered according to this invention will, of course, be determined by the particular circumstances surrounding the case, including, for example, the compound administered, the route of administration, and the condition being treated. A typical daily dose will contain from about 0.01 mg/kg to about 20 mg/kg of the active compound of this invention. Preferred daily doses generally will be from about 0.05 to about 10 mg/kg and ideally from about 0.1 to about 5 mg/kg.

The compounds can be administered by a variety of routes including oral, rectal, transdermal, subcutaneous, intravenous, intramuscular, and intranasal. A special feature of the compound of this invention is that they have high potency and therefore lowered dosages are capable of effectively inhibiting the 5-LO catalyzed reaction.

A variety of physiologic functions have been associated with leukotrienes. As such, the compounds of this invention are believed to have the ability to treat in mammals a variety of disorders associated with leukotrienes such as asthma and allergic diseases, (including allergic rhinitis), inflammatory bowel disease, psoriasis, ischemia, shock, adult respiratory distress syndrome and arthritis. Therefore, the present invention also provides methods of treating the above disorders at the rates set forth above for inhibiting the 5-lipoxygenase catalyzed conversion of arachidonic acid to leukotrienes by administering an asthma, allergic disease, inflammatory bowel disease, psoriasis, shock, ischemia, adult respiratory distress syndrome or arthritis relieving dose of a compound of the present invention.

The compounds of the present invention are preferably formulated prior to administration. Therefore, another embodiment of the present invention is a pharmaceutical formulation comprising an effective amount of a compound of Formula I or a pharmaceutically acceptable salt thereof and a pharmaceutically acceptable carrier, diluent or excipient therefor.

The active ingredient in such formulations comprises from 0.1% to 99.9% by weight of the formulation. By pharmaceutically acceptable it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gumacacia, calcium phosphate, alginates, tragacanth, gelatin, calcium silicate, microcrystalline cellulose, polyvinylpyrrolidone, cellulose, water syrup, methyl cellulose, methylhydroxybenzoates, propylhydroxybenzoates, talc, magnesium stearate and mineral oil. The formulations may additionally include lubricating agents, wetting agents, sweetening agents, flavoring agents, and the like. The compositions of the invention may be formulated so as to provide quick, sustained or delayed release of the active ingredient after administration to the patient by employing procedures well known in the art.

The compositions are preferably formulated in a unit dosage form, each dosage generally containing from about 0.1 to about 500 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way. "Active ingredient," of course, means a compound according to Formula I or a pharmaceutically acceptable salt thereof.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearate acid | 5 |
| Total | 665 mg |

The components are blended and compressed to form tablets each weighing 665 mg.

Formulation 3

An aerosol solution is prepared containing the following components:

|  | Quantity (mg/capsule) |
|---|---|
| Active ingredient | 250 |
| Cellulose, microcrystalline | 400 |
| Silicon dioxide, fumed | 10 |
| Stearate acid | 5 |
| Total | 665 mg |

The active compound is mixed with ethanol and the mixture added to a portion of the propellant 22, collected to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate starch | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, such containing 50 mg of active ingredient per 5 ml dose, are made as follows:

| | |
|---|---|
| Active ingredient | 50 mg |
| Sodium carboxymethyl cellulose Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Sodium alginate | 500 mg |
| Isotonic saline | 1,000 ml |

The solution of the above ingredients generally is administered intravenously to a subject at a rate of 1 ml per minute.

The following experiments were carried out to demonstrate the ability of the compounds of the present invention to inhibit 5-lipoxygenase.

Sensitization procedures

Male, Hartley strain guinea-pigs (200–250 g) were actively sensitized by three injections of ovalbumin (OA, 10 mg/kg). The OA was administered intraperitoneally on Days 1 and 3 and subcutaneously on Day 5. In vitro experiments were performed 21–25 days later.

General In vitro

On the day of the experiment, guinea pigs were killed by asphyxiation with $CO_2$ and the tracheas removed, cleaned of surrounding connective tissue and cut into sprial strips. Each strip was divided in half for paired experiments. Tissues were placed in 10 ml jacketed tissue baths maintained at 37° C. and attached with cotton thread to Grass force-displacement transducers (FT03C). Changes in isometric tension were displayed on a Grass polygraph (Model 7D). Tracheal strips were bathed in modified Krebs' solution of the following composition (millimolar) NaCl, 118.2; KCl, 4.6; $CaCl_2.2H_2O$, 2.5; $MgSO_4.7H_2O$, 1.2; $NaHCO_3$, 24.8; $KH_2PO_4$, 1.0; and dextrose, 10.0. The buffer contained indomethacin (5 $\mu M$) which potentiated the contractions of the cysteinyl leukotrienes (LT) by removing the influence of cyclooxygenase products. The tissue baths were aerated with 95% $O_2$:5% $CO_2$. Tracheal strips were placed under a resting tension of 2 g, and the tissues were allowed a minimal stabilization period of 60 minutes before undergoing experimentation. Bath fluid was changed at 15 minute intervals during the stabilization period.

Concentration-response curves

Cumulative concentration-response curves were obtained from tracheal strips by increasing the agonist concentration in the organ bath by half-log increments while the previous concentration remained in contact with the tissues van Rossum, *Arch. Int. Pharmacodymn Ther.*, 143, 299–330 (1963). Agonist concentration was increased after reaching the plateau of the contraction elicited by the preceeding concentration. One concentration-response curve was obtained from each tissue. To minimize variability between tissues, contractile responses were expressed as a percentage of the maximal response obtained with carbachol (10 $\mu M$), added to the bath at the end of the concentration-response curve. Initially, tissues were challenged with carbachol (10 $\mu M$) following the 60 minute stabilization period to insure tissue viability. After recording the maximal response to the initial carbachol challenge, the tissues were washed and re-equilibrated for 60 minutes before starting the experimental protocol.

Determination of $EC_{50}$ and % Inhibition

To evaluate the effects of novel 5-lipoxygenase inhibitors in the Schultz-Dale reaction, each compound was incubated with the tissues 30 minutes before starting the curves. Vehicle (DMSO) was given to the paired control tissue. Pyrilamine (10 $\mu M$) was added to all baths at this time to block the actions of released histamine. Responses obtained at the antigen concentration of 30 ng/ml were recorded in the absence and presence of drug and percent inhibition was calculated for each pair of tissues. $IC_{50}$ values were determined by linear regression.

LT or carbachol concentration-response curves were used to determine specificity of the agent as a 5-lipoxygenase inhibitor. In these experiments the test compound was incubated as described above. $EC_{50}$ values, which represent the molar concentration of agonist required to induce 50% of maximal response, was determined by linear regression. Differences in $EC_{50}$ values, in the presence and absence of test compound were analyzed by Student's t-test with $P<0.05$ regarded as significant.

In vivo studies

Male Hartley guinea pigs (350–500 g) were passively sensitized against ovalbumin by i.p. administration of 0.3 ml of antiserum 2 days preceeding the experiment. Hyperimmune serum was prepared from actively sensitizing male guinea pigs conditioned with 2 mg of ovalbumin in 50% Complete Freund's Adjuvant i.p. on days 1 and 5. On day 21, the animals were bled and the serum collected and stored at −20° C. On the day of the experiment the passively sensitized guinea pigs were anesthetized with 35 to 40 mg/kg of pentobarbital sodium given i.p. The right jugular vein was cannulated with Tygon microbore tubing (o.d.=03) connected to a syringe for administration of selected drugs. Blood pressure was measured with a Statham pressure transducer connected to a Tygon catheter placed in the left carotid artery. The trachea was cannulated and each animal was ventilated with room air by means of a Harvard rodent respirator set to deliver a tidal volume of 1 ml/100 g body weight with a rate of 60 breaths/minute. Succinylcholine (5 mg/kg) was given i.v. to suppress spontaneous respiration. Intratracheal pressure, an index of total pulmonary resistance, was measured with a Statham pressure transducer connected to a T-tube on the tracheal cannula. Output signals from the pressure transducers were displayed on a Grass polygraph. Body temperature was maintained within normal limits by means of a Deltaphase isothermal pad. Prior to surgery, test compound or vehicle (PEG 400) was administered to each guinea pig by oral gavage and OA challenge was at designated times following oral dosing. The animals were pretreated i.v. with pyrilamine (5 mg/kg), propranolol (1 mg/kg) and indomethacin (10 mg/kg) 5 minutes prior to the OA challenge. OA-induced increase in tracheal pressure was expressed as a percentage of the maximal pressure obtained by clamping the trachea with a hemistat. To determine the effect of each drug, a % inhibition value was calculated from the vehicle and drug treated animals at each concentration tested.

TABLE II

| | Inhibition of 5-LO | |
|---|---|---|
| Example No. | In Vitro $IC_{50}$ μM | In Vivo Percent Inhibition at 30 mg/kg. po. 2 hr. |
| 1 | 2.1 | 78 |
| 2 | 1.0 | 50 |
| 3 | 0.6 | 30[a] |
| 4 | 0.39 | 81 |
| 5 | 1.2 | 76 |
| 6 | 0.62 | 75 |
| 7 | 2.4 | 93 |
| 8 | 1.8 | 51 |
| 9 | 1.0 | 93 |

Note: [a] = dose of 10 mg/kg.

It should be understood that the instant specification and examples are set forth by way of illustration and not limitation, and that various modifications and changes may be made without departing from the spirit scope of the present invention as defined by the appended claims.

We claim:

1. An N-hydroxy-N-urea and thiourea having the Formula:

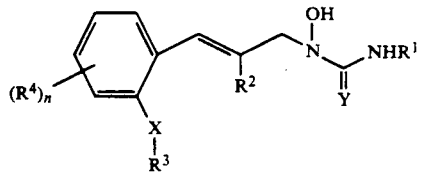

where
X is O or S;
Y is O or S;
$R^1$ is hydrogen, $C_1$-$C_4$ alkyl or $C_3$-$C_8$ cycloalkyl;
$R^2$ is hydrogen or methyl;
$R^4$ is hydrogen or halo;
n is 1 or 2;
$R^3$ is $C_2$-$C_{12}$ alkenyl, $C_3$-$C_{12}$ alkadienyl, $C_4$-$C_{12}$ alkatrienyl, $C_2$-$C_{12}$ alkynyl, $C_4$-$C_{12}$ alkenynyl, $C_3$-$C_8$ cycloalkylmethyl, unsubstituted or substituted styryl, or unsubstituted or substituted phenylethynyl where the phenyl ring of styryl and phenylethynyl may be substituted with one, two, or three of the same or different halo, hydroxy $C_1$-$C_4$ alkyl, $C_1$-$C_4$ alkoxy, $C_1$-$C_4$ alkylthio, trifluoromethyl or trifluoromethoxy; and pharmaceutically acceptable salts thereof.

2. A compound according to claim 1 wherein:
X is S;
Y is O;
$R^1$ is hydrogen or $C_1$-$C_4$ alkyl;
$R^2$ is hydrogen;
$R^4$ is hydrogen or halo;
n is 1 or 2;
$R^3$ is $C_2$-$C_{12}$ alkynyl, or $C_3$-$C_6$ cycloalkylmethyl; and pharmaceutically acceptable salts thereof.

3. A compound according to claim 2 wherein $R^3$ is $C_2$-$C_{12}$ alkynyl and pharmaceutically acceptable salts thereof.

4. A compound according to claim 3 which is selected from:
N-hydroxy-N-urea;
N-hydroxy-N-urea;
N-hydroxy-N-urea;
N-hydroxy-N-urea;
N-hydroxy-N-urea;
N-hydroxy-N-urea, and pharmaceutically acceptable salts thereof.

5. A compound according to claim 4 which is N-hydroxy-N-urea and pharmaceutically acceptable salts thereof.

6. A compound according to claim 2 wherein $R^3$ is $C_3$-$C_6$ cycloalkylmethyl and pharmaceutically acceptable salts thereof.

7. A compound according to claim 6 which is N-hydroxy-N-urea and pharmaceutically acceptable salts thereof.

8. A compound according to claim 6 which is N-hydroxy-N-urea and pharmaceutically acceptable salts thereof.

9. A pharmaceutical composition comprising a pharmaceutically acceptable carrier, diluent or excipient and a compound having the Formula

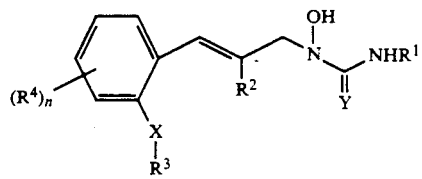

where
X is O or S;
Y is O or S;
$R^1$ is hydrogen, $C_1$-$C_4$ alkyl or $C_3$-$C_8$ cycloalkyl;
$R^2$ is hydrogen or methyl;
$R^4$ is hydrogen or halo;
n is 1 or 2;
$R^3$ is $C_2$-$C_{12}$ alkenyl, $C_3$-$C_{12}$ alkadienyl, $C_4$-$C_{12}$ alkatrienyl, $C_2$-$C_{12}$ alkynyl, $C_4$-$C_{12}$ alkenynyl, $C_3$-$C_8$ cycloalkylmethyl, unsubstituted or substituted styryl, or unsubstituted or substituted phenylethynyl where the phenyl ring of styryl and phenylethynyl may be substituted with one, two, or three of the same or different halo, hydroxy $C_1$-$C_4$ alkyl, $C_1$-$C_4$ alkoxy, $C_1$-$C_4$ alkylthio, trifluoromethyl or trifluoromethoxy; and pharmaceutically acceptable salts thereof.

10. A pharmaceutical composition according to claim 9 wherein:
X is S;
Y is O;
$R^1$ is hydrogen or $C_1$–$C_4$ alkyl;
$R^2$ is hydrogen;
$R^4$ is hydrogen or halo;
n is 1 or 2;
$R^3$ is $C_2$–$C_{12}$ alkynyl, or $C_3$–$C_6$ cycloalkylmethyl; and pharmaceutically acceptable salts thereof.

11. A pharmaceutical composition according to claim 10 wherein $R^3$ is $C_2$–$C_{12}$ alkynyl and pharmaceutically acceptable salts thereof.

12. A pharmaceutical composition according to claim 11 wherein said compound is selected from:
N-hydroxy-N-urea;
N-hydroxy-N-urea;
N-hydroxy-N-urea;
N-hydroxy-N-urea;
N-hydroxy-N-urea;
N-hydroxy-N-urea, and pharmaceutically acceptable salts thereof.

13. A pharmaceutical composition according to claim 10 wherein $R^3$ is $C_3$–$C_6$ cycloalkylmethyl and pharmaceutically acceptable salts thereof.

14. A pharmaceutical composition according to claim 13 wherein said compound is selected from N-hydroxy-N-urea and N-hydroxy-N-urea and pharmaceutically acceptable salts thereof.

15. A method of inhibiting 5-lipoxygenase comprising administering to a mammal in need of 5-lipoxygenase inhibition of 5-lipoxygenase inhibiting dose of a compound having the Formula:

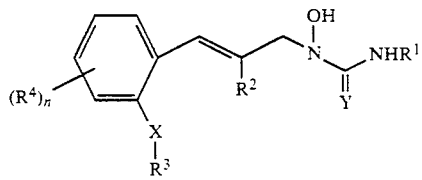

where
X is O or S;
Y is O or S;
$R^1$ is hydrogen, $C_1$–$C_4$ alkyl or $C_3$–$C_8$ cycloalkyl;
$R^2$ is hydrogen or methyl;
$R^4$ is hydrogen or halo;
n is 1 or 2;
$R^3$ is $C_2$–$C_{12}$ alkenyl, $C_3$–$C_{12}$ alkadienyl, $C_4$–$C_{12}$ alkatrienyl, $C_2$–$C_{12}$ alkynyl, $C_4$–$C_{12}$ alkenynyl, $C_3$–$C_8$ cycloalkylmethyl, unsubstituted or substituted styryl, or unsubstituted or substituted phenylethynyl where the phenyl ring of styryl and phenylethynyl may be substituted with one, two, or three of the same or different halo, hydroxy $C_1$–$C_4$ alkyl, $C_1$–$C_4$ alkoxy, $C_1$–$C_4$ alkylthio, trifluoromethyl or trifluoromethoxy; and pharmaceutically acceptable salts thereof.

16. A method of treating asthma, arthritis, allergy, inflammatory bowel disease, psoriasis, shock, adult respiratory distress syndrome or ischemia in a mammal suffering from said condition comprising administering a condition relieving dose of a compound having the Formula:

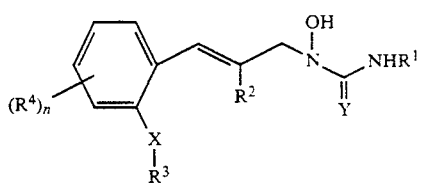

where
X is O or S;
Y is O or S;
$R^1$ is hydrogen, $C_1$–$C_4$ alkyl or $C_3$–$C_8$ cycloalkyl;
$R^2$ is hydrogen or methyl;
$R^4$ is hydrogen or halo;
n is 1 or 2;
$R^3$ is $C_2$–$C_{12}$ alkenyl, $C_3$–$C_{12}$ alkadienyl, $C_4$–$C_{12}$ alkatrienyl, $C_2$–$C_{12}$ alkynyl, $C_4$–$C_{12}$ alkenynyl, $C_3$–$C_8$ cycloalkylmethyl, unsubstituted or substituted styryl, or unsubstituted or substituted phenylethynyl where the phenyl ring of styryl and phenylethynyl may be substituted with one, two, or three of the same or different halo, hydroxy $C_1$–$C_4$ alkyl, $C_1$–$C_4$ alkoxy, $C_1$–$C_4$ alkylthio, trifluoromethyl or trifluoromethoxy; and pharmaceutically acceptable salts thereof.

17. A method according to claim 16 wherein:
X is S;
Y is O;
$R^1$ is hydrogen or $C_1$–$C_4$ alkyl;
$R^2$ is hydrogen;
$R^4$ is hydrogen or halo;
n is 1 or 2;
$R^3$ is $C_2$–$C_{12}$ alkynyl, or $C_3$–$C_6$ cycloalkylmethyl; and pharmaceutically acceptable salts thereof.

18. A method according to claim 17 wherein $R^3$ is $C_2$–$C_{12}$ alkynyl and pharmaceutically acceptable salts thereof.

19. A method according to claim 18 wherein said compound is selected from:
N-hydroxy-N-urea;
N-hydroxy-N-urea;
N-hydroxy-N-urea;
N-hydroxy-N-urea;
N-hydroxy-N-urea;
N-hydroxy-N-urea, and pharmaceutically acceptable salts thereof.

20. A method according to claim 19 wherein said compound is N-hydroxy-N-urea and pharmaceutically acceptable salts thereof.

21. A method according to claim 17 wherein $R^3$ is $C_3$–$C_6$ cycloalkylmethyl and pharmaceutically acceptable salts thereof.

22. A method according to claim 21 wherein said compound is selected from N-hydroxy-N-urea and pharmaceutically acceptable salts thereof.

* * * * *

UNITED STATES PATENT AND TRADEMARK OFFICE
CERTIFICATE OF CORRECTION

PATENT NO.    : 5,130,485                    Page 1 of 4

DATED         : July 14, 1992

INVENTOR(S)   : Gary A. Hite, Edward D. Mihelich, David W. Snyder and Tulio Suarez It is certified that an error appears in the above-identified patent and that said Letters Patent is hereby corrected as shown below:

Col. 19

Claim 1, line 1, "N-hydroxy-N-urea" should read --N-hydroxy-N-[3-(2-substituted phenyl)prop-2-enyl]urea--.

Col. 20

Claim 4, line 3, "N-hydroxy-N-urea" should read --N-hydroxy-N-[3-[2-(2-propynylthio)phenyl]prop-2-enyl]urea--

Claim 4, line 4, "N-hydroxy-N-urea" should read --N-hydroxy-N-[3-[2-(3-butynylthio)phenyl]prop-2-enyl]urea--

Claim 4, line 5, "N-hydroxy-N-urea" should read --N-hydroxy-N-[3-[2-(2-butynylthio)phenyl]prop-2-enyl]urea--

Claim 4, line 6, "N-hydroxy-N-urea" should read --N-hydroxy-N-[3-[2-(2-propynyloxy)phenyl]prop-2-enyl]urea--

Claim 4, line 7, "N-hydroxy-N-urea" should read --N-hydroxy-N-[2-methyl-3-[2-(2-propynylthio)phenyl]prop-2-enyl]urea--

Claim 4, line 8, "N-hydroxy-N-urea" should read --N-hydroxy-N-[3-[3-fluoro-2-(2-propynylthio)phenyl]prop-2-enyl]urea--

Claim 5, line 2, "N-hydroxy-N-urea" should read --N-hydroxy-N-[3-[2-(2-propynylthio)phenyl]prop-2-enyl]urea--

Claim 7, line 2, "N-hydroxy-N-urea" should read --N-hydroxy-N-[3-[2-(cyclohexylmethylthio)phenyl]prop-2-enyl]urea--

Claim 8, line 2, "N-hydroxy-N-urea" should read --N-hydroxy-N-[3-[2-(cyclopropylmethylthio)phenyl]prop-2-enyl]urea--

UNITED STATES PATENT AND TRADEMARK OFFICE
CERTIFICATE OF CORRECTION

PATENT NO.    :    5,130,485

DATED         :    July 14, 1992

INVENTOR(S)   :    Gary A. Hite, Edward D. Mihelich, David W. Snyder and Tulio Suarez It is certified that an error appears in the above-identified patent and that said Letters Patent is hereby corrected as shown below:

Col. 21

Claim 12, line 3, "N-hydroxy-N-urea" should read --N-hydroxy-N-[3-[2-(2-propynylthio)phenyl]prop-2-enyl]urea--

Claim 12, line 4, "N-hydroxy-N-urea" should read --N-hydroxy-N-[3-[2-(3-butynylthio)phenyl]prop-2-enyl]urea--

Claim 12, line 5, "N-hydroxy-N-urea" should read --N-hydroxy-N-[3-[2-(2-butynylthio)phenyl]prop-2-enyl]urea--

Claim 12, line 6, "N-hydroxy-N-urea" should read --N-hydroxy-N-[3-[2-(2-propynyloxy)phenyl]prop-2-enyl]urea--

Claim 12, line 7, "N-hydroxy-N-urea" should read --N-hydroxy-N-[2-methyl-3-[2-(2-propynylthio)phenyl]prop-2-enyl]urea--

Claim 12, line 8, "N-hydroxy-N-urea" should read --N-hydroxy-N-[3-[3-fluoro-2-(2-propynylthio)phenyl]prop-2-enyl]urea--

Claim 14, lines 2 and 3, "N-hydroxy-N-urea" should read --N-hydroxy-N-[3-[2-(cyclohexylmethylthio)phenyl]prop-2-enyl]urea--

Claim 14, line 3, "N-hydroxy-N-urea" should read --N-hydroxy-N-[3-[2-(cyclopropylmethylthio)phenyl]prop-2-enyl]urea--

Claim 15, line 3, "inhibition of 5-lipoxygenase" should read --inhibition a 5-lipoxygenase--

Col. 22

Claim 19, line 3, "N-hydroxy-N-urea" should read --N-hydroxy-N-[3-[2-(2-propynylthio)phenyl]prop-2-enyl]urea--

Claim 19, line 4, "N-hydroxy-N-urea" should read --N-hydroxy-N-[3-[2-(3-butynylthio)phenyl]prop-2-enyl]urea--

UNITED STATES PATENT AND TRADEMARK OFFICE
CERTIFICATE OF CORRECTION

PATENT NO. : 5,130,485

DATED : July 14, 1992

INVENTOR(S) : Gary A. Hite, Edward D. Mihelich, David W. Snyder and Tulio Suarez It is certified that an error appears in the above-identified patent and that said Letters Patent is hereby corrected as shown below:

Col. 22

Claim 19, line 5, "N-hydroxy-N-urea" should read --N-hydroxy-N-[3-[2-(2-butynylthio)phenyl]prop-2-enyl]urea--

Claim 19, line 6, "N-hydroxy-N-urea" should read --N-hydroxy-N-[3-[2-(2-propynyloxy)phenyl]prop-2-enyl]urea--

Claim 19, line 7, "N-hydroxy-N-urea" should read --N-hydroxy-N-[2-methyl-3-[2-(2-propynylthio)phenyl]prop-2-enyl]urea--

Claim 19, line 8, "N-hydroxy-N-urea" should read --N-hydroxy-N-[3-[3-fluoro-2-(2-propynylthio)phenyl]prop-2-enyl]urea--

Claim 20, line 2, "N-hydroxy-N-urea" should read --N-hydroxy-N-[3-[2-(2-propynylthio)phenyl]prop-2-enyl]urea--

UNITED STATES PATENT AND TRADEMARK OFFICE
CERTIFICATE OF CORRECTION

PATENT NO. : 5,130,485

DATED : July 14, 1992

INVENTOR(S) : Gary A. Hite, Edward D. Mihelich, David W. Snyder and Tulio Saurez It is certified that error appears in the above-indentified patent and that said Letters Patent is hereby corrected as shown below:

Col. 22

Claim 22, line 2, "N-hydroxy-N-urea and pharmaceutically acceptable salts thereof." should read --N-hydroxy-N-[3-[2-(cyclohexylmethylthio)phenyl]prop-2-enyl]urea and N-hydroxy-N-[3-[2-(cyclopropylmethylthio)phenyl]prop-2-enyl]urea and pharmaceutically acceptable salts thereof.--

Signed and Sealed this

Thirty-first Day of August, 1993

Attest:

BRUCE LEHMAN

Attesting Officer

Commissioner of Patents and Trademarks